United States Patent [19]

Heurte

[11] Patent Number: 5,360,015
[45] Date of Patent: Nov. 1, 1994

[54] APPARATUS FOR STUDY AND REEDUCATION OF THE ANKLE

[76] Inventor: Alain Heurte, 6, rue de la Fontaine, F-29239 Gouesnou, France

[21] Appl. No.: 700,197

[22] Filed: May 15, 1992

[30] Foreign Application Priority Data

Oct. 13, 1989 [FR] France ............... 89 13651

[51] Int. Cl.⁵ .............................................. A61B 5/103
[52] U.S. Cl. .................................. 128/779; 128/774; 128/782; 482/79; 33/515
[58] Field of Search ............. 128/774, 779, 782, 25 B, 128/25 R; 482/8, 66, 68, 79, 80, 146; 273/449; 434/258; 33/512, 515

[56] References Cited

U.S. PATENT DOCUMENTS

| | | | |
|---|---|---|---|
| 3,712,294 | 1/1973 | Muller | 128/782 |
| 3,870,297 | 3/1975 | Elder | 482/146 |
| 4,199,137 | 4/1980 | Giguére | 482/79 |
| 4,463,946 | 8/1984 | Wallace et al. | 482/8 |
| 4,705,271 | 11/1987 | Mondloch et al. | 482/112 |
| 4,944,309 | 7/1990 | Mechling | 128/782 |
| 5,042,504 | 8/1991 | Huberti | 128/779 |
| 5,049,079 | 9/1991 | Furtado et al. | 434/253 |
| 5,052,406 | 10/1991 | Nashner | 128/782 |
| 5,080,109 | 1/1992 | Arme, Jr. | 128/782 |
| 5,211,163 | 5/1993 | Mortenson | 128/781 |

FOREIGN PATENT DOCUMENTS

| | | | |
|---|---|---|---|
| 1021818 | 11/1977 | Canada . | |
| 2641183 | 7/1990 | France | 128/779 |
| 1372342 | 10/1974 | United Kingdom . | |

Primary Examiner—Stephen C. Pellegrino
Assistant Examiner—Guy V. Tucker
Attorney, Agent, or Firm—Laff, Whitesel, Conte & Saret

[57] ABSTRACT

The apparatus has a plate (1) pivotingly mounted on a horizontal axis (X—X') with stops (4) limiting the inclination of the plate (1) on either side of the axis. The inclination of the plate is measured at (7) and recorded at (14). Display (17) displays the values recorded in recorder (14). The stops (4) are adjustable. The measuring device comprises an electric potentiometer (7) servocontrolled by the motion of the plate (1) about its pivoting axis (X—X'). An associated electric voltage or current measuring apparatus has output which is applied to an analog-digital converter (10) having an output connected to the input (12) of a first digital data memory (14).

4 Claims, 2 Drawing Sheets

APPARATUS FOR STUDY AND REEDUCATION OF THE ANKLE

The present invention relates to an apparatus for the study and reeducation of the ankle.

BACKGROUND

With respect to the apparatuses for reeducation of the ankle, the state of the technique may be illustrated by documents DE-A-227 571; GB-A-1 372 342, FR-A-2 502 492, FR-A-2 535 209, U.S. Pat. No. 4,605,220 and the French Patent Application No. 88 1-2928 filed on Sep. 28, 1988 by the present Applicant. All of these apparatuses have a plate mounted pivoting on a ball and socket joint or a type of half ball. They make it possible, especially, to permit a pathologic ankle to recover its propioceptive properties, but they give the reeducator and the patient only subjective information; the reeducator looks as the ankle reacts and trusts in his personal experience, and the patient trusts in the sensations he feels.

SUMMARY OF THE INVENTION

The object of the present invention consists in providing an apparatus capable of bringing numerical informations that can be interpreted by the reeducator. The numerical informations obtained with the apparatus according to the invention make it possible, for one thing to compare the condition of the pathologic ankle with that of the healthy ankle of the patient and, for the other thing, to follow the evolution of the applied therapy.

According to a characteristic of the invention, there is provided an apparatus comprising a plate mounted pivoting on a horizontal shaft, with lug pieces that limit the slant of the plate, means for recording the values given by said measuring means, and means for posting the values recorded in said recording means.

According to another characteristic, the lug pieces are regulatable.

According to another characteristic, the measuring means are an electric potentiometer controlled by the displacement of the plate around its pivoting shaft and associated with an apparatus for the measurement of the electric current or voltage, the output of which is connected to an analog-numerical converter the output of which is connected to the input of a first memory for numerical data.

According to another characteristic, the apparatus further comprises an electronic flip-flop the output of which is also connected to a second memory for numerical data, the posting means being simultaneously connected to the outputs of the first and of the second data memory.

According to another characteristic, the apparatus further comprises a device for the numerical measurement of the-electric potentiels collected by sensors applied on muscles, the numerical output of the device being connected to a third numerical data memory, the posting means being such that they can be selectively simultaneously connected to the outputs of the first, second and third memories.

According to another characteristic, the posting means are a screen of a microcomputer that also has a time base connected to said screen, to said memories and to its central control unit.

The above-mentioned characteristics of the invention as well as others will clearly appear upon reading of the description of one exemple of execution, said description being given with respect to the attached drawing in which:

DESCRIPTION OF PREFERRED EMBODIMENT

Figure 1:
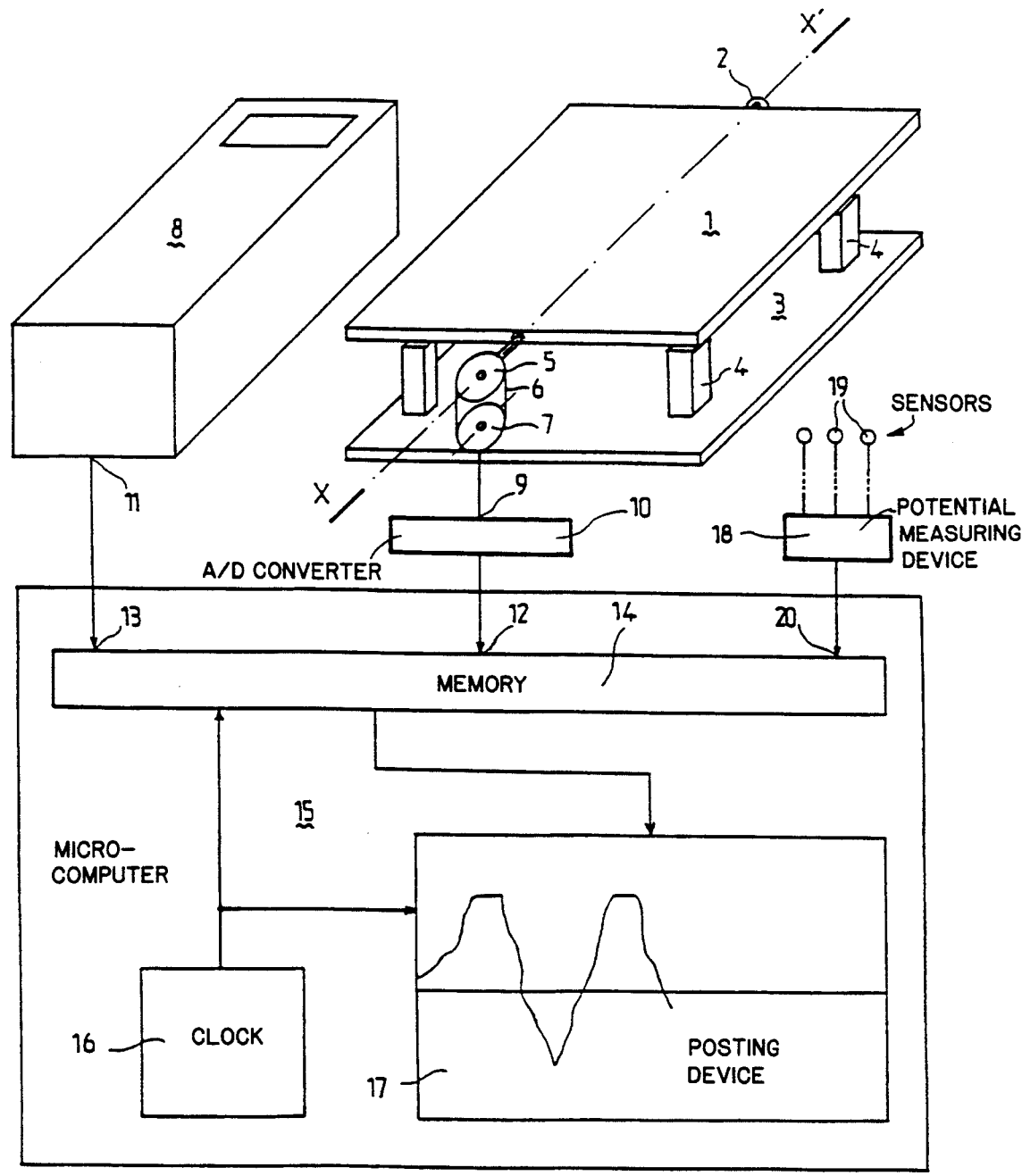
FIG. 1 is a schematic view of the apparatus according to the invention.

The apparatus in FIG. 1 comprises a plate 1 mounted on a horizontal shaft X—X', itself mounted on bearing posts 2, one of which only is visible, the feet of which are fixed on a base 3. Vertical lug pieces 4 arise from base 3 under plate 1 to limit the slant of that plate around shaft X—X'. Preferably the lug pieces 4 are adjustable in length. On shaft X—X', in front of plate 1, there is mounted a pulley 5 over the groove of which there runs a string 6 that drives potentiometer 7 into rotation. The rotations of potentiometer 7 algebraically duplicate those of plate 1 around shaft X—X', and the sides of base 3 that are parallel to shaft X—X' can be connected by springs that increase the stability of plate 1. These springs may be constituted by adjustable elastic stretchers.

In the example in FIG. 1, close to assembly 1-2-3 there is placed an electronic balance 8. The relative positions of the assembly 1-2-3 and of the balance 8 are such that a person can have one foot, the right foot here, on assembly 1-2-3 and the other foot, the left foot here on the balance 8, with a standing position completely normal. He/she can put more weight on one foot than on the other.

The wires 9 of potentiometer 7 are connected to the input of an analog-digital converter 10. The output of converter 10 and the output 11 of the balance 8 respectively are connected to the inputs 12 and 13 of a memory 14 that is a part of a microcomputer 15. The latter comprises a source of direct current, not shown, that makes it possible to feed potentioneter 7.

The microcomputer 15, in addition to its logical central control unit, not shown, has a time base 16 and a posting device 17 in the form of a cathode ray screen. The time base 16 synchronizes the operations of memory 14 and of the posting device 17.

Under control of the logical unit of the microcomputer 15, the data entered into memory 14 and that simultaneously come from the potentiometer 7 and from the balance 8, may be posted in the form of two curves.

The apparatus according to the invention preferably is completed by a device 18 for the measurement of potentials, equipped with sensors 19 to which it is connected by wires. Such a device is classical. The sensors are applied to muscles, to the lateral peroneus for example. Depending on the state of work of the muscle, the corresponding electrode collects a different potential that is detected and measured in device 19, and numerized. The output of device 18 is connected to the input 20 of memory 14.

In practice, the device 18 is used to observe the activity of the peroneus, for example, during the movement of an ankle. When the material shown in FIG. 1 is used, it is assumed that, for example, the left foot is the healthy foot and the right foot is the pathologic one. In that case, it is obvious that the patient tends to put his entire weight, or at least more weight, on the foot placed on the balance 8. That practically is the initial position. The reeducator asks the patient to put more weight on plate 1 the position of which is unstable around shaft X—X'. During a first time period, the patient succeeds in compensating for that instability by bringing plate 1 back to its horizontal position as soon as it moves away from it. Then, later, the weight applied to plate 1 increasing, the instability shows itself by a sudden slant of the plate, until the latter meets the top of lug pieces 4, either on one side or on the other. The patient then can bring back most of the weight to the balance 8. During that phase, the angular displacements of the plate were recorded by means of potentiometer 7 and, simultaneously, the remaining weight applied to the balance is also recorded. It is known, by observing the weight curve, when the patient started to push down on plate 1. It is known when he stopped controlling the plate and what was then the weight he was applying to it. A study of the curves enables the reeducator to draw conclusions from them.

The data delivered by the device 18 also make it possible to know when the muscles began to act, after the beginning of the unbalance, and when they stopped working, after balance has been regained.

It is possible to turn the patient around, so that he will have his good foot on the plate and his bad foot on the balance. The measurements made, as indicated above, make it possible to assess the quality of the good foot, knowing that such quality will define the goal to be reached for the reeducated foot.

It is also possible to cause assembly 1-2-3 to function by itself, the two feet of the patient bearing on plate 1, symmetrically relative to the shaft X—X' for example.

The initial position then is the left foot, assuming that it is the normal one, that slants the plate by pressing on lug pieces 4 on the left side. The patient causes an increase of weight on the right foot. Once equilibrium has been reached, plate 1 becomes unstable and, after a short while it slants against the lug pieces on one side or on the other, mostly on the side of the normal foot. An examination of the lengths of time during which the plate is unstable makes it possible to follow the reeducation.

Figure 2:
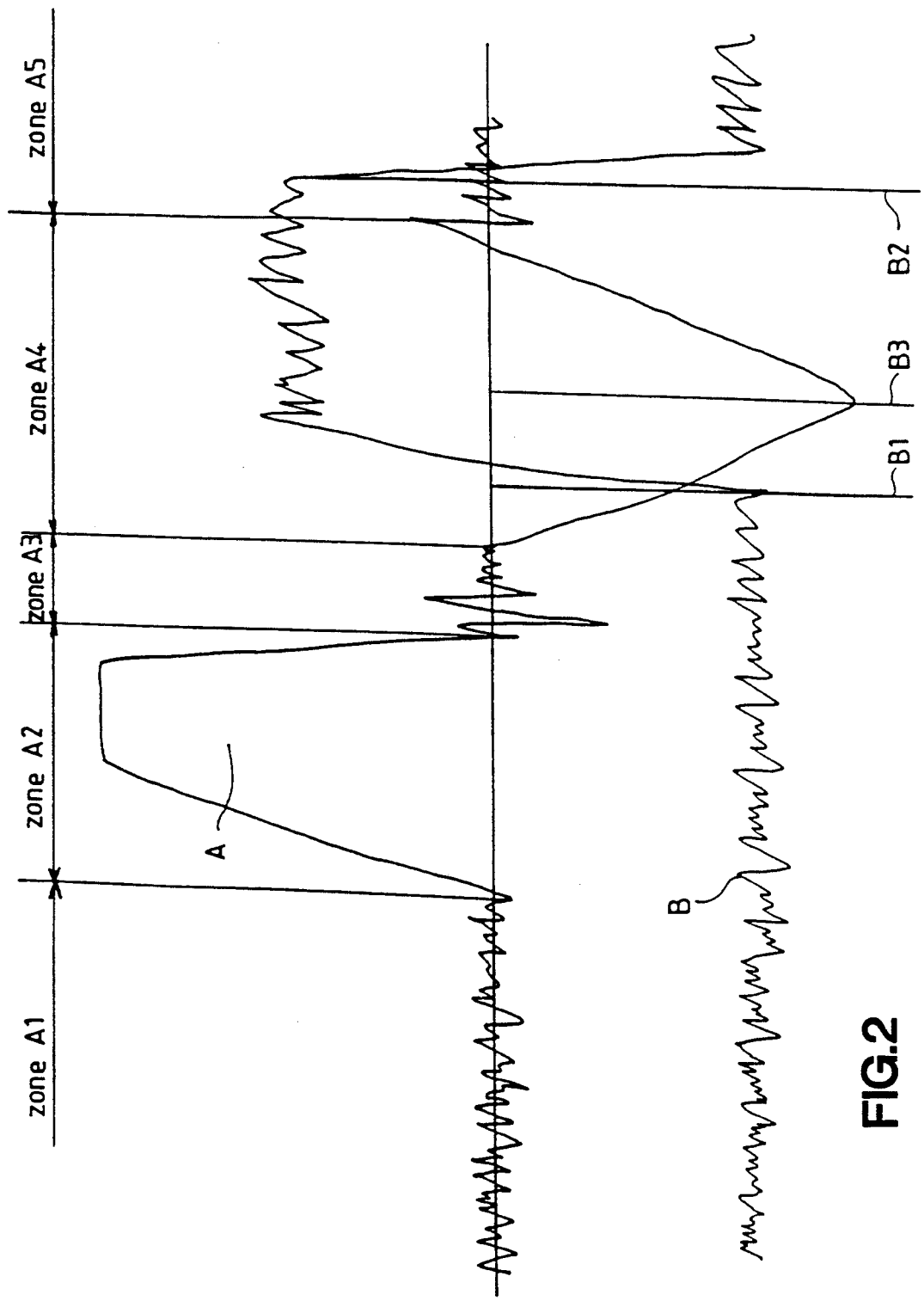
FIG. 2 is a curve shown on the posting means of the apparatus.

In FIG. 2, there are shown the shapes of two curves A and B, during a lack of equilibrium the two feet of the patient resting on the plate, as defined above. Curve A shows the evolution of the slant of the plate around a position with zero slant shown by the straight line Y—Y' that, in the representation, is merged with the time axis.

In a first zone A1, the plate supposedly is in equilibrium. In a second zone A2, the weight is on the healthy foot and the plate, that bears on the corresponding lug pieces 4, is motionless. In a third zone A3, a part of the weight is brought back, by the pathologic foot, onto the right (side) of the plate and equilibrium is reached; in a fourth zone A4 there is lack of equilibrium and the plate slants toward the right. In a fifth zone A5, it comes back toward equilibrium and remains there.

Curve B shows the evolution of the activity of a lateral peroneus muscle during the lack of equilibrium shown by curve A. During the zones A1, A2 and A3, the muscle is at rest, this being shown by the almost horizontal appearance of the curve. With some delay relative to the start of zone A4, as shown by the vertical B1, the muscle becomes active and it remains so until the return to equilibrium, or approximately so, as shown by the vertical (line) B2. Between the vertical (lines) B1 and B2 there is shown a vertical B3, that indicates the time when the muscle ceases to brake the slanting by performing excentric work to pass to the time of winning control when it performs concentric work.

Looking at the zones A1 to A5 and at the positions of the vertical (lines) B1 to B3 makes it possible to assess the condition of the ankle.

Of course, the foot or feet may rest on the plate in directions others that the one parallel to shaft X—X'.

I claim:

1. A system for measuring the articulation and assessing the function of a human ankle, said system comprising a plate (1) mounted on a shaft to pivot about a horizontal axis (X—X'), said plate (1) forming a means for receiving a first foot associated with the ankle being assessed, a base (3), said shaft having ends which are rotatably secured to said base (3), at least one post (4) mounted on said base (3) for limiting the pivoting motion of said plate (1) about the horizontal axis (X—X'), a weighing instrument (8) for receiving the other foot of a patient whose ankle is being assessed and giving value outputs responsive to the weight placed thereon, means (7) for measuring and giving value outputs responsive to the angular amount of pivoting motion of said plate (1) responsive to motion of said first foot, memory means (14) having a first input (12) for storing said values received from said measuring means (7), said memory means having a second input (13) for storing said values received from said weighing instrument (8), said memory means giving an output representing said stored values, and means (17) for displaying said output representing values received at the first (12) and second (13) inputs of said memory means (14).

2. A system according to claim 1 wherein the measuring means comprises an electric potentiometer (7) controlled by the angular amount of displacement of plate (1) about said shaft (X—X') in association with a means for the measurement of an electric current or voltage through said potentiometer, the output of said measuring means being connected to an analog-digital converter (10) the output of which is connected to supply digital data to the first input (12) of said memory means (14).

3. A system according to claim 1 and further comprising a plurality of sensors (19), means (18) for making a numerical measurement of electric potentials collected by said sensors (19) when applied to the patient's muscles, a numerical output of said numerical measurement means (18) being connected to a third input (20) to said memory means for storing numerical data, the display means (17) being selectively and simultaneously connected to the outputs of the first, second and third memories.

4. A system according to claim 3 wherein said display means is part of a microcomputer (15) containing said memory means, said memory means having (14) three memory zones that are individually associated with the first, second and third inputs to said memory, respectively, and the display means is formed by a screen (17) of the microcomputer (15).

* * * * *